United States Patent [19]

Pfanzelt

[11] 4,418,267

[45] Nov. 29, 1983

[54] PROTECTION APPARATUS

[76] Inventor: Josef Pfanzelt, Forstenrieder Allee 17, 8000 Munchen 71, Fed. Rep. of Germany

[21] Appl. No.: 260,771

[22] Filed: May 5, 1981

[30] Foreign Application Priority Data

May 6, 1980 [DE] Fed. Rep. of Germany ....... 3017215
May 6, 1980 [DE] Fed. Rep. of Germany ....... 3017241

[51] Int. Cl.³ .............................................. B23K 9/32
[52] U.S. Cl. ........................................... 219/147; 2/8
[58] Field of Search ............... 219/147, 132; 2/8, 427, 2/432

[56] References Cited

U.S. PATENT DOCUMENTS 3,159,844 12/1964 Haboush ............................ 219/147
3,227,866 1/1966 Peters et al. ....................... 219/147
3,838,247 9/1974 Finger et al. ...................... 219/147
4,241,286 12/1980 Gordon .............................. 219/147

FOREIGN PATENT DOCUMENTS 224784 4/1943 Switzerland ....................... 219/147

Primary Examiner—C. C. Shaw
Attorney, Agent, or Firm—Robert E. Burns; Emmanuel J. Lobato; Bruce L. Adams

[57] ABSTRACT

An automatic electrically operated protective system protects a welder from harmful light rays and sputtering emanating from the weld zone. An electric circuit controls a light shield means to assume either an open or closed condition. The electric circuit is responsive to the absolute value of the voltage between a welding electrode and a workpiece. A light shield opening signal is produced when this value is smaller than the electrode open circuit voltage but greater than the maximum electrode welding voltage upon ignition of the arc. A light shield closing signal is produced prior to the ignition of an arc when the aforementioned value is greater than the electrode to workpiece short circuit voltage and slightly smaller than the electrode open circuit voltage.

15 Claims, 7 Drawing Figures

PROTECTION APPARATUS

FIELD OF INVENTION

The present invention relates to an electrical-automatic system for use in conjunction with electric welding apparatus to protect against the harmful optical and mechanical effects of the welding arc light by the use of an electrical switching arrangement which is either mechanical (by means of a spring biased electromagnetic system) or electronic (by means of polarizers influenced by electrical voltage) to activate a light shield between the welding zone and the operator.

BACKGROUND OF THE INVENTION

The use of effective and dependable protection devices (hand shield, protective helmet) in working with electric welding apparatus has been a present need since the beginning of this technique, as is apparent from the patent literature in the form of different proposals for such protective devices. According to the general progress of the technique, apparatus with electro-automatic function have been in the foreground. With such apparatus, a light shield is changeable between open and closed condition by means of an electomagnetic system which is either mechanical or is electro-optical, by means of a depolarizer (liquid crystal), whereby the closed condition of the light shield, according to modern practice without exception, is activated by a photoelectric element responsive to the light intensity in the welding zone. While the known protecting devices are in accord with the opinion of a competent specialist, it has been found that in practice they do not work satisfactorily and are subject to many difficult disadvantages.

The most serious disadvantage to which all known devices are subject without exception is that electrical signal for controlling the light shield to its closed condition comes too late, so that the welder is subjected to light exposure which, because of its being partially in the ultraviolet range, is harmful even though it is short. In the case of welding work over a long period of time, the continual exposure to the light flashes each time the welding arc is ignited can frequently lead to irreversible eye damage. Moreover, the failure of the light shield to close sufficiently quickly can lead to mechanical damage of the eyes or to sight scars of the welder through sputtering in the weld area. Relevant statistics of the employer's liability insurance of all industrial countries gives the information that the number of such injuries with the resultant liability is disturbingly high.

A further significant disadvantage of the above-mentioned delayed control of the light shield in going to its closed condition is a possible decrease in the quality of the weld because the welder, partially through anxiety with respect to the expected light flash, and partially because of the glare, does not hold the welding electrodes in exact position and thereby the weld area becomes unclean and requires expensive corrective work.

The cause for the delayed control of the light shield lies in the above-mentioned use of a photoelectric element producing a closing signal. Such an element can, logic-wise, first respond when the arc light has already reached a harmful level and thus comes inevitably too late to close the light shield in time, quite apart from the fact that to this already delayed signal must be added the time constant for operation of the light shield elements. To explain these most difficult disadvantages of known arrangements briefly and in other words, the harmful arc light must first occur before a closing signal for the light shield can be produced. With the use of photoelectric equipment for producing the closing signal for the light shield, satisfactory operation cannot be obtained regardless of cleverness in the modification of the electrical and/or mechanical part of the protection device.

The above-mentioned serious disadvantages apply to all previously known examples in the patent literature relating to protective devices and, in particular:
1. CH-PS No. 393 632
2. CH-PS No. 562 607
3. FR-PS No. 7409611
4. DT-OS No. 2 550 559
5. GB-PS No. 834 021
6. UP-PS No. 2 423 320
7. DT-AS No. 2 315 308
8. FR-PS No. 73 10949
9. US-PS No. 3,540,058
10. DE-OS No. 2.349.794
11. GB-PS No. 1,077,096

Of these known arrangements, items 1-6 and 11, which work with a mechanical light shield, have other serious faults in addition to the above-mentioned disadvantage of a delayed closing signal. In particular, with an electromagnetic system for moving the light shield from its normal open position to a closed position, the operation is either much too sluggish by reason of the long stroke of the magnet armature when the viewing area is of a practical useful size or, alternatively, the viewing area must be reduced to an extremely small window in order to reduce the stroke of the magnet armature. The dimensioning of the electromagnet is in accordance with the following rule: If the magnet is made correspondingly large for a sufficient stroke of the light shield, it is unusably heavy and, moreover, its time contant is such that the light shield cannot be closed quickly enough. If the magnet is made correspondingly small for a small stroke of the light shield, its time constant is indeed shorter, but the force of the magnet is not strong enough for timely control of the light shield weight. These physical principles are unalterable and condemn all prior electromagnetic solutions of previously known construction and mode of operation to failure. Moreover, there is no provision for preventing reopening of the sight shield when the welding arc, during the welding operation, is extinguished for a very short time, and again struck, as is often the case by reason of irregular burning off of the electrodes, or from drawing too long an arc.

Moreover, also with known protection devices with an electronically controlled light shield, i.e., with a depolarizer (liquid crystal) controlled with an electrical voltage, there exist significant disadvantages making it impossible to guarantee satisfactoy operation even if the signal for controlling the light shield to its closed condition were not delayed. The widely held and completely understandable assumption that with the use of such electronic light shield all problems of mechanical light shields would be automatically solved, is in many respects false. In particular, such depolarizers, in any case according to the present worldwide stand of the technique, have a time constant which is far greater than the relatively short time period required for true protection of the eyes. Thus, even in the most favorable cases, the time constant of such depolarizers is approximately 80 to 100 ms, whereas, for true protection of the eyes, the time period for operation of the light shield must be less than 10 ms. The proof of this is found in the relevant technical literature, as well as in data sheets of the producers of liquid crystals and, moreover, also in recent prospectuses of producers of protection equipment of this kind. Moreover, such liquid crystal light shields do not have the necessary filtering properties, in particular against the particularly harmful ultraviolet rays of a welding arc such as those of dark glass such as normally are used in the welding technique, and, furthermore, they do not repel the likewise harmful infrared rays. On account of the much too slow reaction time of liquid crystal light shields, and their insufficient filtering and damping qualities, the following compromise has been proposed. Half of the viewing window of the protecting device is provided with a liquid crystal layer, and the other half is provided with a changeable dark glass in the usual manner. However, as the liquid crystal layer remains transparent for the above-mentioned time period of about 80 to 100 ms. after ignition of the welding arc, and hence provides no protection for the eyes, damping filter discs are provided. The whole arrangement thus has the unforeseen disadvantages, firs, that when beginning a weld, the viewing window does not have fully transparency and permits only a greatly damped view of the weld area by reason of the filter discs, and, second, after ignition of the welding arc, the welder must change his eye position from the free view zone to the dark glass, which makes necessary a new search for the welding area proper and can lead to an impairment of the weld quality. Thus, as long as there is no fluid crystal which can change its optical condition in less than 10 ms, from full transparency to a condition in which it has effective filtering properties for the harmful rays of the welding arc, such electronic protecting system can provide no optimal solution to the long existing problem.

SUMMARY OF THE INVENTION

Proceeding from the state of the art described above, the present invention provides a protection device of the first named type, which, by avoiding the described disadvantages of previously known arrangements, and with correct design and over-all arrangement, achieves timely change of the light shield to its closed condition. According to the invention, this is obtained by controlling the light shield by an electrical threshold value switch which, on switching values analogous to the absolute values of the electrode circuit in such manner that it is switched to open the light shield by an absolute value of the voltage in the welding electrode circuit which is smaller than the electrode open circuit voltage but greater than the maximum electrode welding voltage upon ignition of the welding arc, and is switched to close the light shield when the absolute value of the electrode circuit voltage is greater than the electrode short circuit voltage, but preferably only slightly smaller than the electrode open circuit voltage.

In principle, control signal could be derived also from the current characteristic or from the magnetic behaviour of the welding apparatus, but research has disclosed that this is connected with several grave disadvantages. In particular, if either a transformer or magnetic coupling with the welding electrode circuit, or a contact inside the welding apparatus itself is necessary, this would be difficult and expensive. Moreover, a solution of this kind would not be universally useable because the current and magnetic characteristics of different welding apparatuses are not the same. Furthermore, in most welding machines containing transformers and/or condensers, the current is delayed due to phase angle.

On the other hand, with the control signal derived from the voltage characterisitc of the welding electrode circuit in accordance with the present invention, several important advantages are obtained. In the first place, the voltage levels in the welding electrode circuit corresponding to the electrode open circuit voltage, the electrode short circuit voltage, and the voltage produced by ignition of the welding arc are easier to ascertain and plot than the uncontrollable welding current which may vary between the wide limits of 5 and 800 A. On the other hand, the voltage curves of the welding electrode circuit of different types of welding apparatus are relatively uniform, so that protective devices in accordance with the present invention can be realized for all types of welding apparatus in an advantageous and economical manner. In particular, however, the voltage reflex in the welding electrode circuit is extraordinarily rapid and exact, so that a light shield controlling signal can be produced and processed before the arc light is ignited. Moreover, the coupling of the switching arrangement with the welding apparatus itself can be effected quickly and easily without getting into the welding apparatus because the welding electrode circuit in each case is freely accessible. Moreover, it is particularly advantageous that with the electrical coupling of the protection device with the electrode voltage circuit of the welding apparatus, all problems relating to observance of safety regulations for the contact voltage are automatically eliminated because the corresponding requirements must have been already fulfilled by the producer of the welding apparatus in order to make the welding electrode circuit shockproof. Moreover, the need of providing a special current source, or additional electrical elements, such as safety transformers for coupling to the current circuit of the welding apparatus, such as heretofore required, is automatically eliminated through feeding the protective device from the welding electrode circuit because the welding electrode circuit, on the one hand, provides a stable current source and, on the other hand, the electrode open circuit voltage does not exceed a predetermined safe value.

Advantageously, according to a preferred embodiment of the invention, the threshhold value switch is formed as an electronic threshhold value switch on the basis of a Schmitt trigger which is fed indirectly from the electrode voltage and is trimmed with a Zener diode of a practically constant response value. Its signal input is through a potentiometer coupled with the electrode voltage, and its signal output controls the load circuit for the light shield either directly or through a transistor. This threshhold value switch assures a universally useable design and function in principle of the protecting device independently of the variable absolute value of the voltage of the welding electrode circuit.

An early release of the closing signal before ignition of the welding arc light is assured, when, according to an embodiment of the invention, the switching arrangement for controlling the light shield comprises a signal switch coupled with the electrode voltage, which by being independent of the variable absolute value of the electrode voltage and from the duration of a voltage reduction in the welding electrode circuit, produces a positive or negative control signal upon a relatively very small reduction in electrode circuit voltage of the order of one percent of the electrode open circuit voltage. The construction and operation of this signal switch, according to the circuit diagram shown in the drawings, cannot be surpassed with respect to the desired voltage sensibility and economy of time, and represents an optimal solution of this portion of the problem.

It is known that in electric welding there is occasionally a short interruption of the welding arc, followed immediately by reignition, for example, by reason of the electrode spacing being too great, or unequal electrode burning. With prior protection devices, such short interruption in the welding arc can lead to undesired opening of the light shield before termination of the welding process and thereby to eye injury. This can reliably be avoided if, according to an example of the invention, the switching arrangement for controlling the light shield contains a time delay circuit with the help of which the control of the light shield to effect its return to open position after an interruption (opening of the threshhold value switch) is delayed. At the same time, this seves the further purpose that the welder is protected from the rays emitted by the weld zone for a short time after the end of the welding process, so that he cannot look on the still white hot welding area, nor can be injured through occasional splattering from the weld zone in the first stage of cooling. Thus, through such delay, the light shield is first brought to its open position and thereby again provides a free view of the weld area only when the above-mentioned sources of danger are eliminated.

It is advantageous, when the protection device is so designed, that the current supply for the switching arrangement to control the light shield, independently of the kind of current of the welding apparatus, is generally provided by one or more input bridge rectifiers fed from the welding apparatus because this makes possible an economical uniform construction and electrical function of the protection device, regardless of the kind of power supply of the welding apparatus. If the welding apparatus operates with direct current, this passes through the input rectifier unaltered as a direct current voltage whereas alternating current is rectified so that on the output side a uniform DC voltage for the protecting device is available.

As already mentioned, the protecting device, in accordance with the invention, can have a mechanically as well as an electronically controlled light shield. However, in view of the above mentioned disadvantages of an electronically controlled light shield, it appears in agreement with the basic purposes of the invention to use a mechanically controlled light shield, at least with the provision that, in accord with the early control signal, it operates sufficiently rapidly. This is assured when the light shield is operatively coupled with the armatures of two solenoids which, upon excitation, move the armatures guided by non-magnetic guide tubes against a spring force. In comparision to electromagnets with closed iron cores, such as those used in known arrangements, solenoids have an essentially smaller time constant, which is advantageous in securing the quickest possible response to the closing signal. Moreover, the armature can have a relatively large stroke without appreciable reduction of the magnet force, so that the light shield can be moved beween relatively wide limit positions to provide a good view of the weld zone.

The required increase in the closing speed of the light shield to attain a closing time less than about 10 ms, as required to provide true protection against injury, is only possible through a construction and mode of operation which departs basically from heretofore known arrangements. In accordance with an embodiment of the invention, this is obtained by a construction so arranged that the closed position of the light shield is identical with its mechanical rest position in which it is held by spring force. When the solenoids are energized, the light shield is moved from closed position to open position agains the spring force. After the solenoids are deenergized, the light shield is returned by spring force to the closed position. According to a further feature of this embodiment of the invention, the field strength of the solenoids is increased during the time the light shield is being moved from a closed position to open position and is then reduced to a value which is only slightly greater than that required to retain the light shield in open position. Through this mode of operation, which is contrary to that of known protection devices, it is assured first that the time constant of the magnet system, which may be several seconds, no longer plays any role, since the solenoids do not move the light shield to closed position but, rather, move it to open position and, second, that it is possible to use a smaller and lighter magnet system, but with a relatively large stroke to provide a large viewing area in comparison with former systems, very strong return springs being usable, so that the closing of a light shield no longer depends on the time constant of the magnet system but rather on the spring constant of the return spring. Moreover, a third advantage is that if there is any defect of switch system, for example, by reason of a current failure or otherwise, there is constant protection against the arc rays—in contrast to heretofore known arrangements—because, in the event of any such defect, the return spring automatically brings the light shield to its closed position. Moreover, this mode of operation automatically provides a constant repeatable control of the component parts and their function because, after putting the welding apparatus into operation, as well as after each welding interval, the light shield can only be opened to provide a free view of the weld area when the electrical and magnetic components are in order. An optimal protective function of the apparatus is thereby assured.

Since the time constant of the magnet system plays no role in the closing of the light shield, the solenoid, according to an embodiment of the invention, can be provided with an auxiliary iron circuit serving as a magnetic flux path. However, such circuit is not closed and in no position of the armature is it in direct ferromagnetic contact with such iron circuit. In this manner, the solenoid, without having any closed iron circuit with corresponding remanence upon deenergization of the solenoid, is essentially strengthened so that correspondingly strong return springs can be used. This leads to a further shortening of the time period for the return of the light shield to its closed position.

A further embodiment of a protective device in accordance with the present invention using a mechanically controlled light shield, uses for moving the light shield, preferably in a partly rotation movement, a micro-electric motor controlled by the switching arrangement and having a speed reducing drive for moving the light shield to its open position against a relatively strong return spring. The light shield is held in open position by an automatically operating catch until the control signal coming from the switching arrangement opens the catch by means of an electromagnet and allows the light shield to be moved rapidly to its closed position through the action of the return spring. This mode of control of the light shield can be used within the frame of the present invention and has an advantage over the above described magnet system in that only a very small voltage of the order of 1.5 to 2.5 volts is required for driving the micro-electric motor, and, moreover, through the use of a reducing drive, it is possible to use a strong return spring which will move the light shield to closed position in an extremely short time period of the order of 1 to 2 ms.

The electrical connection between the welding apparatus on the one hand and the protective device in accordance with the present invention on the other hand, can, according to the invention, be made in a manner that, for the electrical coupling between the welding electrode circuit and the switching arrangement, there are provided two coupling cables having at one end an insulated plug socket for connection with a plug of the switching arrangement and, at the other end, contact points in an insulating socket which pierce through the electrode cables approximately parallel to the conductors of the electrode cables. This mode of connection is particularly advantageous for applying the protective device to existing welding equipment because it is universally usable with all types of welding apparatus and because, moreover, the installation of the protective device can be carried out in an extraordinarily simple and quick manner.

According to a further feature of the invention, it is expedient for the connecting cable between the housing containing the switching arrangement and the protective device containing the light shield, to be made by a flexible cable insulated with heat-resistant material, for example, fibreglass braided tubing resistant to temperature up to 600° C. This heat-resistant protective tubing provides long-lasting protection to the connecting cables against mechanical and electrical defects through heat or glowing weld particles.

According to a further feature of the invention, there is provided additional means for providing a closing signal for the light shield before the ignition time of the welding arc. This can be in the form of a microphone in a welding helmet near the mouth of the wearer or a contact near the thumb on the hand grip of a hand shield, so that a signal produced by sound waves or by the touch contacts is transmitted to the signal input of an operational amplifier of the switching arrangement, the output signal of which, over the threshhold switch, effects the return of the light shield to its closing position. Through this additional arrangement, the invention on the one hand provides an increased security relative to the early closing signal for the light shield to a desired point of time prior to ignition of the welding arc and, on the other hand, with basically the same construction of the protective device, gives the possibility of assuring an early closing signal when the apparatus is used independently of welding apparatus, for example, in rolling mills, foundries, optical laboratories, laser laboratories, etc.

BRIEF DESCRIPTION OF DRAWINGS

The nature, objects, and advantages of the invention will be more fully understood from the following description of a preferred embodiment, illustrated by way of non-limiting example in the accompanying drawings, in which.

DESCRIPTION OF PREFERRED EMBODIMENT

Figure 1:
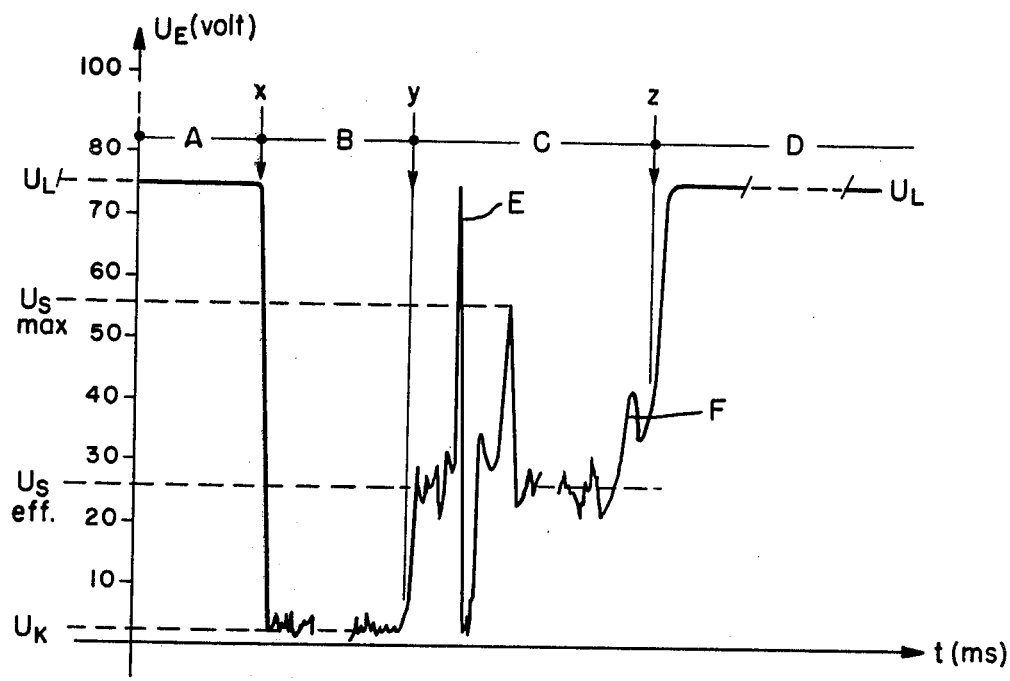
FIG. 1 is a curve showing the voltage characteristics in the welding electrode circuit of welding apparatus.

In the diagram shown in FIG. 1, the ordinate represents the amplitude of the electrode voltage $U_E$ of welding apparatus and the abscissa represents time. $U_L$ represents the electrode open circuit volage, $U_K$ represents the electrode short circuit voltage upon contact of the welding electrode with the welded work piece, $U_{S\ eff.}$ represents the normally effective electrode welding voltage, and finally, $U_{S\ max}$ represents the maximum welding voltage during the welding operation by reason of a short interruption of arc. Of these voltages, the open circuit voltage $U_L$ can have an absolute value between about 40 V≅AC or DC, and a maximum of 100 V=DC. The short circuit voltage $U_K$ varies with different welding apparatuses depending on the welding material and the type and properties of electrodes in the range between 0.5 V and 5 V. The effective welding voltage $U_{S\ eff.}$ usually has a value between 18 V and 30 V and is, as shown in FIG. 1, not linear, but fluttering according to the welding material and the relative height of the welding arc. As is also clearly visible from FIG. 1, the maximum welding voltage $U_{S\ max}$ can rise considerably according to the height of the welding arc and in some instances may approach the value of the open circuit voltage $U_L$. When the electrodes are applied at point of time x; i.e., the welding electrodes are brought into metallic contact with the work piece, the voltage drops to the values of the short circuit voltage $U_K$. This zone of the application of the welding electrodes is designated "B". When the electrodes are raised at point of time y, the voltage in the electrode circuit rises to the value of the welding voltage having a mean value of $U_{S\ eff.}$ However, through short extinction and reignition of the welding arc, as happens sometimes in practice, for example, through too great electrode spacing, the voltage can rise to a peak "E" approaching open circuit voltage $U_L$, and then, upon the beginning of reignition of the arc, drops for a short time to the value near the short circuit voltage $U_K$, finally passing into effective circuit voltage $U_{S\ eff.}$ The range "F" designates the voltage amplitude which occurs upon withdrawal of the welding electrodes at the end of the welding operation. Upon complete withdrawal of the welding electrodes at the point of time z, at the end of the welding operation, the voltage rises again to the open circuit voltage $U_L$. The time period of the welding operation is designated in FIG. 1 by the range "C". The time period designated "D" corresponds to the rest period of the welding apparatus before the next weld, or before being switched off. As previously mentioned, the illustrated voltage range is uniform for all electrical welding apparatuses, whereby with different types of apparatus, there are merely different absolute values of the voltage amplitude.

Figure 2:
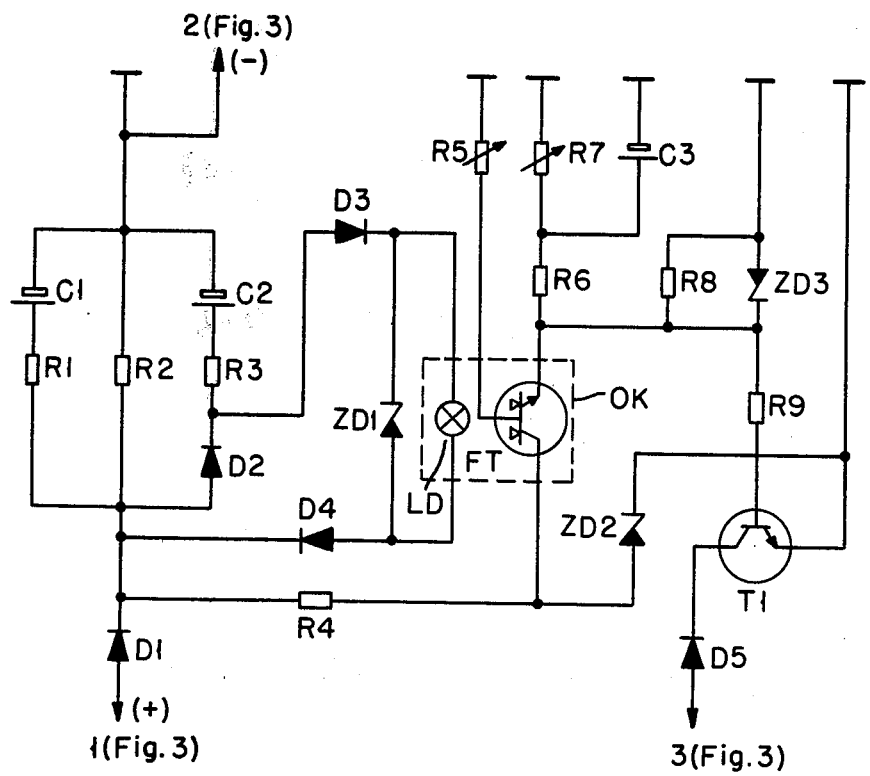
FIG. 2 is a circuit diagram of a switching circuit for producing an early closing signal for the light shield.
Figure 3:
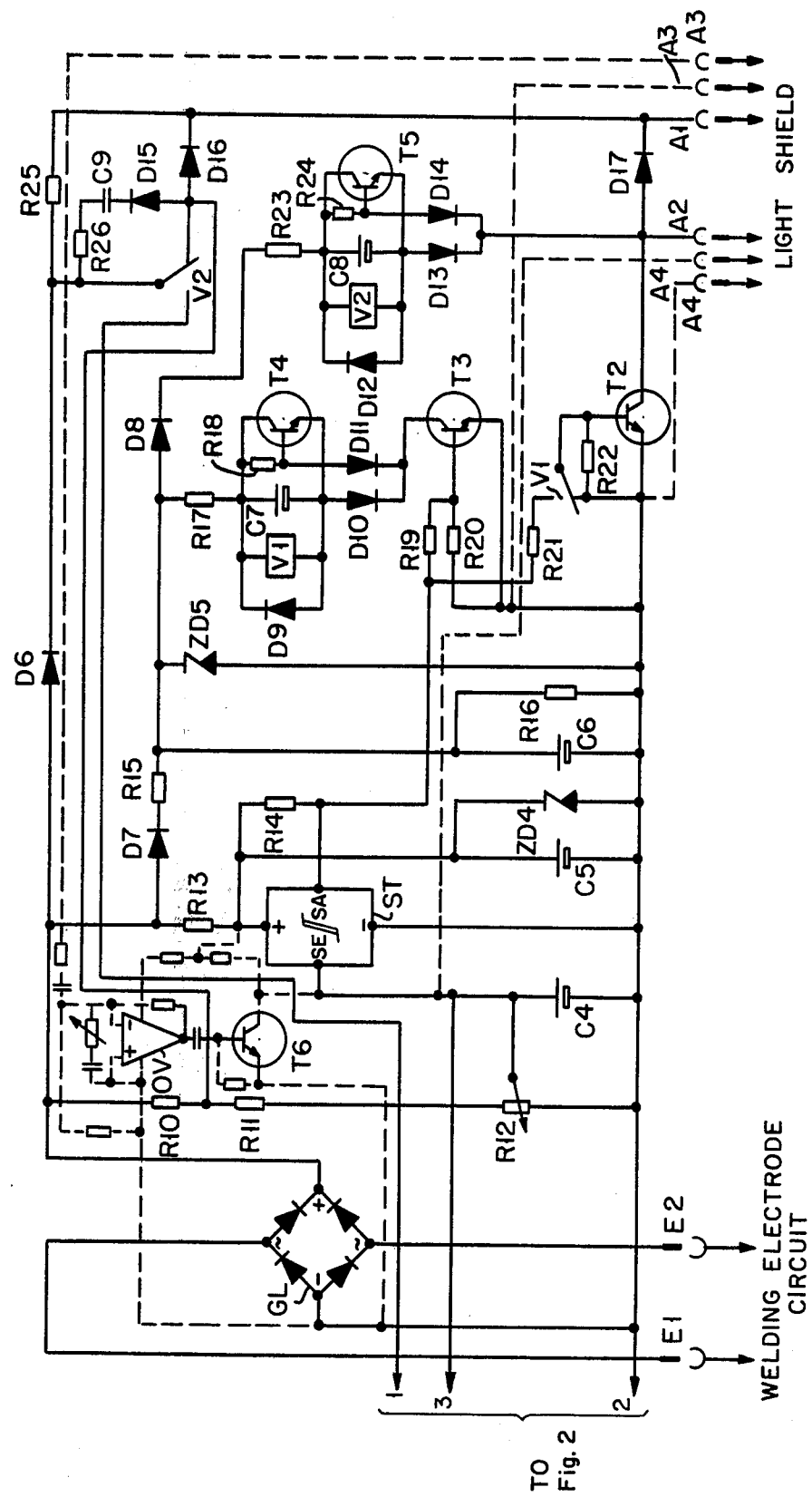
FIG. 3 is a circuit diagram of a control circuit responsive to the voltage characteristics illustrated in FIG. 1.

In the drawings, terminals 1, 2, and 3 of FIG. 2 are connected respectively with terminals 1, 2, and 3 in FIG. 3. If the signal switch circuit shown schematically in FIG. 2 is turned on through terminals 1 and 2 by the closing of the relay contacts V2 in FIG. 3, both capacitors C1 and C2 are charged to the same potential by voltage from the rectifier GL in FIG. 3 and, hence, from the welding electrode circuit E1, E2 in FIG. 3, the voltage being transmitted over 1-D1-R1-C1-2 and 1-D1-D2-R2-C2-2, respectively. An effective current over the parallel-switched circuit of the optical coupler OK does not occur because the two diodes D3, D4 are in closed condition and are at the same voltage level. A possible minimal current through the light diode LD of the optical coupler OK produced by the voltage drop across the diode D2 will be eliminated through the connection of the base of the phototransistor FT to minus over the high ohmic variable resistance R5. The phototransistor FT of the photocoupler OK is thus closed so that the capacitor C3 is discharged to minus over the variable resistance R7 and the switch transistor T1 is likewise closed. The signal switch is thus in closed waiting condition with charged capacitors C1, C2.

If, with the switch circuit in this condition (for example, at time point x in FIG. 1), the voltage in the welding electrode circuit is reduced only slightly (for example, in FIG. 1 from the selected open circuit voltage $U_L = 75$ V to 74.5 V), this effects a corresponding discharge of both capacitors C1, C2 to a corresponding new voltage. However, only the capacitor C1 can be discharged at once over the resistors R1+R3 to minus while the capacitor C2 cannot discharge over the resistor R3 because the diode D2 is closed. The equalization of charge of capacitor C2 can occur over R2-D3-LD-D4-R3 to minus. The light diode LD in the photocoupler OK is thereby energized whereby the parallel-connected Zener diode ZD1 protects the light diode against undue voltage peaks. The rays of the light diode LD act on the base of the phototransistor FT, so that it becomes conductive and thereby connects the base of the switch transistor T1 with plus through 1-D1-R4-collector of FT-emitter of FT-R9. The transistor T1 thereupon becomes conductive and connects terminal 3 of the signal switch circuit with minus through the emitter of T1-collector of T-1 and D5. This minus potential on the terminal 3 is transmitted to the signal input (SE) of the threshold value switch (ST in FIG. 3) and there effects a closing of the threshold value switch and consequently a transfer of the light shield to its closed position.

Of the other components of the signal switch circuit shown in FIG. 2, the resistor R6 serves as a protective load for the charging of capacitor C3. The variable resistor 7 serves for discharging the capacitor C3 to minus. The capacitor C3 serves to store the sometimes very short control signals coming from the photocoupler OK. The resistor R8 in cooperation with the base resistor R9 of the transistor T1 serves as a voltage divider, and, finally, the Zener diodes ZD2 and ZD3 serve as protection against unduly high voltage peaks in the base circuit or collector-emitter circuit of the switching transistor T1.

The circuit shown in FIG. 3 can best be understood from the following description of its operation.

Figure 5:
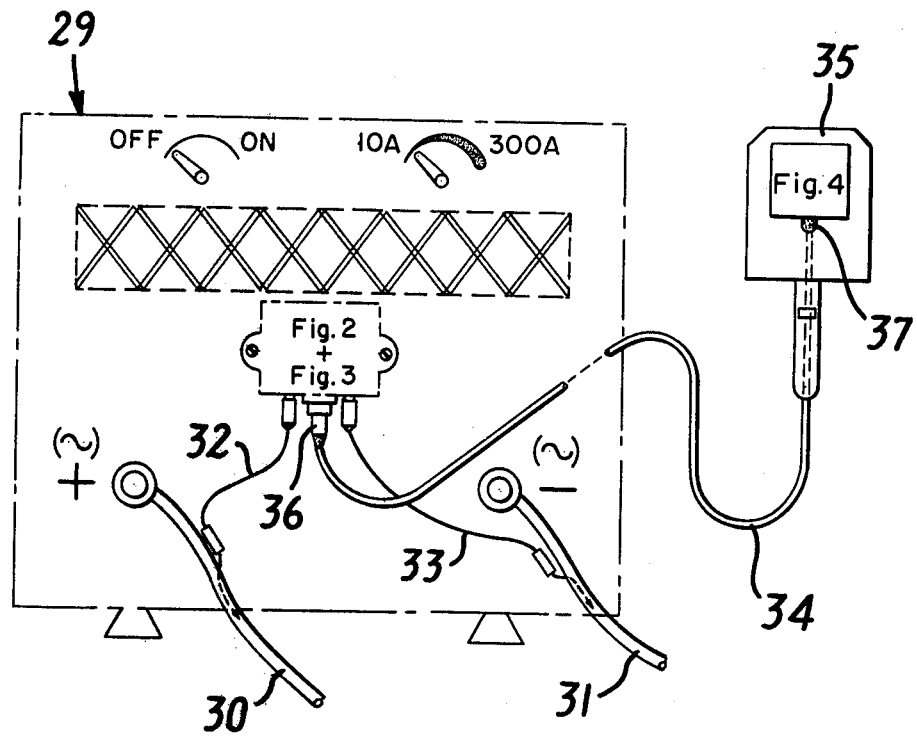
FIG. 5 is a schematic view of welding apparatus with a protective device in accordance with the present invention.

If, as shown schematically in FIG. 5, the electrical voltage of the welding electrode circuit is connected to the input terminals E1, E2 (for example, through coupling cables shown in FIG. 6), the voltage is rectified by the input rectifier GL and constitutes a +/− supply voltage for the circuit components. The value of this supply voltage is practically identical with the welding electrode voltage and, with known electric welding apparatus, usually has a value between 55 V and 75 V. However, it can have a maximum value of up to 100 V and, for small hand welding apparatus and so-called "boiler" welding apparatus, may have a minimum value of 42 V. This supply voltage, through a current limiting resistor R13, feeds the threshold value switch ST (Schmitt-trigger) which, by means of a Zener diode ZD4 with a harmonic smoothing capacitor C4, is adjusted to a constant response value independently of the variable absolute value of the supply voltage. As soon after the welding apparatus has been switched on, as the voltage applied to the input SE of the threshold switch ST through the voltage divider comprising the resistance combination R10, R11, R12 exceeds a predetermined value set by means of the potentiometer R12 which is greater than the amplitude of the effective welding voltage, but smaller than the electrode open circuit voltage, the threshold switch circuit ST is activated to supply a + signal at its signal output SA. It is not necessary for each protection device to make an individual adjustment of the potentiometer R12, it being sufficient according to the aforementioned usual voltage levels of known welding apparatus for the threshold switch circuit to be set for a voltage between the usual maximum welding voltage of about 30 V and the minimum open circuit voltage of 42 V, thus, for example, about 35 V. The + signal supplied by the output terminal SA of the threshold voltage switch, is supplied through a voltage divider R19, R20 to the base of a switch transistor T3 so that this transmits the minus of the supply voltage over its emitter to its collector. The mini relay V1 is thereby energized through the circuit comprising plus feed voltage -D7-R17-V1-D10-collector of T3-emitter of T3-minus feed voltage. However, operation is delayed until the capacitor C7 connected in parallel with the relay V1 is charged with a correspondingly high voltage.

This time delay serves a purpose which will later be described. The switching transistor T4 is closed because the plus voltage transmitted through the base resistor R18 is connected directly to minus thrugh diode D11 and transistor T3. If the relay V1 operates to reverse its switch contact v1, the positive voltage coming from the signal output SA of the threshold switch circuit ST is led through the resistor R22 to the zerobiased base of the switching transistor T2 so that this becomes conductive. Thereby, the closed light shield (for example, according to FIG. 4), is energized through the plus feed voltage -D6-v2-D16-A2-collector of T2-emitter of E2-minus feed voltage, which, as shown schematically in FIG. 5 is connected through terminal elements A1, A2, and the connecting cables 34 so that the light shield opens and permits free view of the weld area. With a magnetically controlled light shield as shown by way of example in FIG. 4, this excitation is effected undamped with full supply voltage and with a winding dimension for short time over-excitation, so that by the opening of the light shield a relatively strong return spring can be tensioned. With such a magnet system, high inductive voltage peaks which would be damaging to the switching transistor T3 can be short circuited by a freerunning diode D17 connected in a closing direction.

With the closing of the transistor T2, the mini relay V2 is also excited through the circuit consisting of the plus supply voltage -D7-D8-R23-V2-D13-collector of T2-emitter of T2-minus supply voltage. However, the mini relay V2 is delayed by means of the capacitor C8, so that V2 can operate only if C8 is sufficiently charged. Here also, the switching transistor T5 is closed because its base is connected to a minus supply voltage through diode D14 and the transistor T2. The two diodes D9 and D12 serve to protect the transistors T4 and T5 against inductive voltage peaks which can arise from the windings of relays V1 and V2. In case the welding machine produces an alternate current supply and the supply voltage from the input rectifier GL is full wave rectified but not smoothed, a capacitor C6 with a load resistance R15 and an unloading resistance R16 is provided in order to provide the relay circuit with a clean direct current. Since, however, the threshold value switch circuit ST switches upon input of a closing signal without time delay, a diode D7 is provided which blocks the discharge of the capacitor C7 over the threshold value switch ST. Moreover, there is provided a Zener diode ZD 5, which limits and holds constant the supply voltage in both relay circuits V1/C7 and V2/C8 independently of the variable value of the supply voltage on the permissible relay voltage (e.g. 24 V). A diode D8 blocks the reverse charging of the capacitor C8 over the delay circuit V1/C7.

If the mini relay V2 operates and reverses its switch contact V2, a plus supply voltage can be fed to a terminal A1 only over the current limiting resistor R25, whereby the voltage for the magnet system for moving the light shield, connected with terminals A1, A2 is reduced to a value which is only sufficient to retain the light shield in open position so that the over-excitation of the magnet system during opening of said light shield is switched off. The diodes D6 and D16 in the above mentioned current path block a possible reverse voltage from the magnet system of the light shield on the signal input SE of the threshold value switch ST. The resistor R26 connected in parallel with the relay contact V2 in conjunction with the capacitor C9 forms a sparkless path to protect this contact during the short time it is in the load circuit of the magnet system moving the light shield. Of course, said means V2, R26, C9, D15 may be eliminated by using a switch transistor, the collector and emitter of which overbridge the limit resistor R25 and which is controlled over its base depending upon the positions of contact V 2.

A diode D15, connected in series with this spark suppressor, serves to prevent a supply current from flowing through the diode D16 after reversal of the switch contact v2 which must then pass through the resistor 25. When the switch contact v2 reverses, voltage is applied to the signal switch shown in FIG. 2 over the circuit comprising plus feed voltage -D6-v2-terminal 1 in the manner described above and the signal switch is thereby activated. There follows an inactive waiting period of the protective device as indicated by the period D in FIG. 1, during which the light shield is open.

If, after this waiting period, the welding electrodes are applied so as to produce a closing signal in the signal circuit illustrated in FIG. 2 in the manner already described, i.e., a minus voltage applied on terminal 3 on the switching arrangement illustrated in FIG. 3, such signal is applied to the signal input SE of the threshold value switch circuit ST and closes this, i.e., the latter produces a minus voltage at the signal output SA. Hereby, the minus voltage is applied to the switching transistor T2 through SA-R21-v1-base of T2, whereby this quickly closes and the voltage on the light shield is removed so that the light shield is quickly closed by the operation of the return spring pretensioned by the opening of the light shield. Simultaneously, the transistor T3 is closed through the circuit consisting of SA-R19-base T3, whereby the capacitor C7, under the action of its own positive voltage charge over the resistor 18 on the base of T4, is rapidly discharged to minimum capacity through the switching transistor T4 and the diode D9. Thereby, the relay V1 is deenergized, whereby its switch contact v1 is reversed and the base of transistor T2 is switched for safety to a minus voltage. Simultaneously, by reason of the closing of the transistor T2, the minus voltage for the relay circuit V2/C8 is cut off so that the capacitor C8 is also discharged by means of the base resistor R24 over the transistor T5 and the diode D12. The switch contact V2 is thereby returned to the rest position shown on the drawing. The protective device remains in this switch position throughout the entire welding process, whereby signals of the threshold value switch circuit ST produced through short control signals of the signal switch cannot become effective by reason of the time delay created through the switch circuit V1/C7, i.e., a new switching of transistor T2, and thereby an opening of the light shield can occur only when after a short time delay the relay contact V1 is again in active position.

If, after the end of the welding operation the weld electrodes are fully withdrawn and the supply voltage again rises to open circuit value, the switching arrangement is again activated as already described only after a time delay effected through the circuit V1/C7, i.e., the transistor T2 again becomes conductive and the light shield is again opened until there is a new closing signal or the entire welding apparatus is switched off. The starting position is thereby attained.

For producing a closing signal for the protective shield any desired time before ignition of the welding arc, the protective system may comprise a microphone M in a protective helmet near the user's mouth or a contact switch K in a protective handheld shield near the user's thumb. If said microphone M is activated by sound from the user's mouth, a small voltage is produced, which is amplified by a known amplifier (integrated circuit) OV, the output of which produces a positive signal to the base of a switch transistor T6 changing said positive signal to a minus signal for the input SE of the threshold value switch ST. This minus signal produces a minus signal on the output SA of the threshold value switch ST and, as already described, transistor T2 (FIG. 2) is opened and terminals A1-A2 connected with the magnet system moving the protective light shield are closed. The elements around the amplifier OV and transistor T6 are necessary electric elements well known for controlling of OV and T6 and hence they are not described.

If instead of a microphone, a hand-moved switch K mounted in a hand-held shield is used, by turning on this switch a minus signal is switched on the input SE of threshold value switch ST and therefore, as already described, the magnet system moving the light shield immediately is deenergized and the light shield is moved rapidly to its closed position by the power of the described return springs. Terminals A3–A4 are for connection between the protective system circuit shown in FIG. 3.

Figure 4:
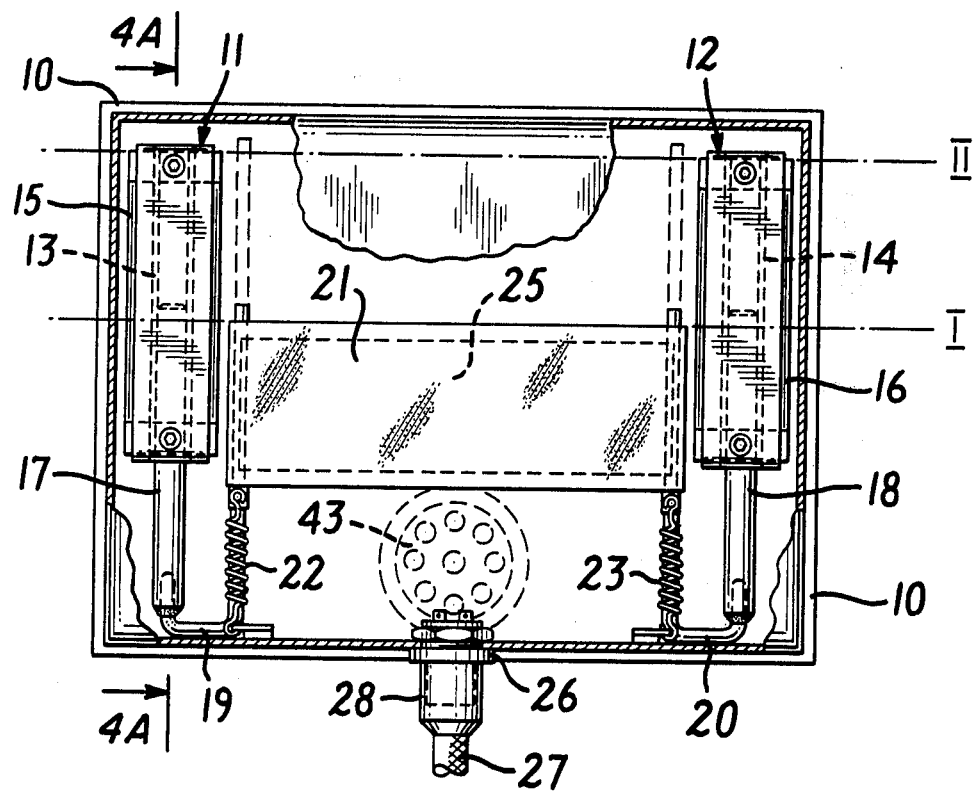
FIG. 4 is an elevation partially in vertical section of an electrically operated light shield in accordance with the invention.
Figure 4A:
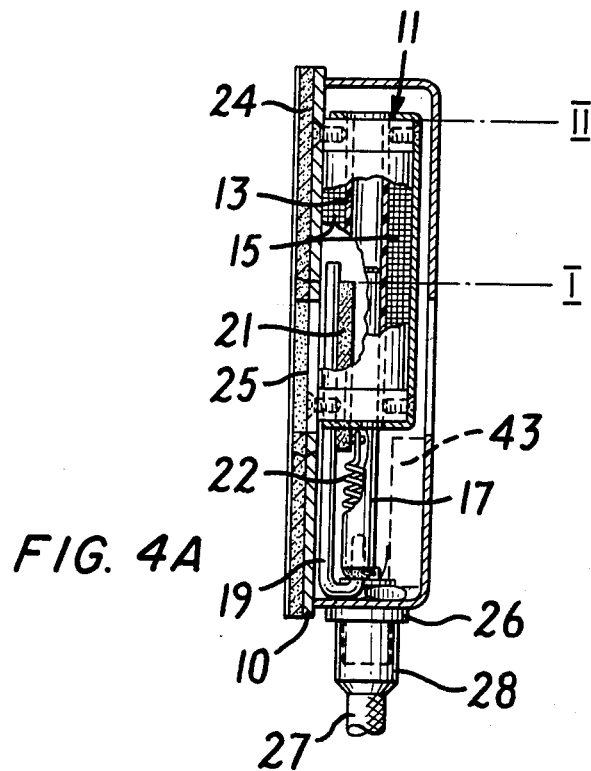
FIG. 4A is a cross-section taken approximately on the line 4A—4A in FIG. 4.

In FIG. 4 there is shown by way of example a magnetically controlled light shield with a chassis plate 10 on which two solenoids 11 and 12 are fixedly mounted. Each of the solenoids 11 and 12 comprises a coil 15, 16 on an axially extending guide tube 13, 14 of non-magnetic material. Two armatures 17, 18 of paramagnetic material are slidable in the above-mentioned guide tubes 13, 14. Upper ends of the armatures 17-18 are preferably coated with non-magnetic material while coupling members 19, 20 of non-magnetic material are fixedly secured to the lower ends. The coupline members are generally U-shaped and have upwardly extending legs to which a light shield 21 of usual dark glass is secured. Strong return springs 22, 23 having upper ends attached to the light shield 21 and lower ends anchored to the chassis plate, hold the light shield 21, the two armatures 17, 18 and the connecting members 19, 20 in a rest position designated I in FIG. 4. This rest position is identical with the closed position of the light shield, i.e., the shield 21 in position I closes the free window 25 provided in usual manner in a plate of dark glass 24 secured on the chassis plate 10. A plug socket 26 mounted on the chassis plate has contacts which are connected with terminals of both of the windings 15-16 of the solenoids and with contacts of a plug 28 of a connecting cable 27, as clearly shown in FIG. 5. When the sindings of the solenoids are energized, the armatures 17, 18 are drawn into the solenoids and the shield 21 is thereby moved to the position designated II in FIG. 4 which corresponds to the open position and permits a free view of the weld area through the window 25. When the solenoids are deenergized, the return springs 22, 23 bring the shield 21 quickly back to the position I and the window is thereby closed by the dark glass light shield. Number 43 represents a crystal microphone mounted in the chassis plate 10.

In FIG. 5, there is shown schematically an electric welding apparatus 29 having output terminals to which two welding electrode cables 30, 31 are connected. From these, coupling cables 32, 33, shown in more detail in FIG. 6, extend to a housing containing the switching arrangement according to FIGS. 2 and 3. From this switching arrangement, a two conductor flexible cable 34 extends to the protective device proper 35 (hand shield or protective helmet) in which is mounted a light shield as shown by way of example in FIG. 4. The flexible cable 34 is preferarably covered with a heat-resistant glass fiber braided tubing. To facilitate the demountability of the individual parts of the protective arrangement, the connecting cable 34 is preferably provided at its ends with plug-in fittings 36, 37.

Figure 6:
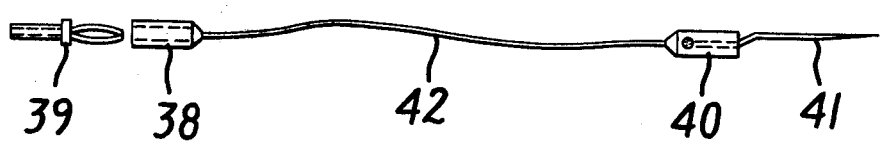
FIG. 6 is a schematic view of the coupling of the protective device to the welding apparatus.

A coupling cable for connecting the switching arrangement of FIGS. 2 and 3 with the welding electrode cables 30, 31 as shown by way of example in FIG. 6, consist of a single conductor flexible cable 42 having at one end a socket 38 for connection with a plug 39 mounted in the housing of the switching arrangement. At the other end of the cable 42 there is an isolating socket 40 with a pointed contact spike 41 which can be stuck into the welding electrode cable so as to engage and extend approximately parallel to the cable conductor. Thus, the welding apparatus does not need to be provided with any special fittings for connection to the protective device of the present invention.

What I claim is:

1. The combination with electric welding apparatus comprising welding electrodes and a welding electrode circuit, an automatic electrically operated protective system for protecting a welder from harmful light rays and sputtering emanating from the welding zone, said system comprising an electrically controlled light shield means changeable from an open condition in which it permits a free view of the weld area and a closed condition in which it blocks harmful light rays and particles projected from the weld area, and an electric circuit controlling said light shield means, said electric circuit means comprising threshold value switching means having an output coupled with said light shield means and an input coupled with said welding electrode circuit, said threshold value switching means being responsive to switching values analogous to the absolute values of the electrode circuit voltage, to produce at its output a light shield opening signal when the absolute value of the voltage in the welding electrode circuit is smaller than the electrode open circuit voltage but greater than the maximum electrode welding voltage upon ignition of the welding arc, and to produce a light shield closing signal, prior to the ignition of an arc, when the absolute value of the electrode circuit voltage is greater than the electrode short circuit voltage and only slightly smaller than the electrode open circuit voltage.

2. A protective system according to claim 1, in which said threshold value switching means comprises a Schmitt trigger having a signal input coupled with the welding electrode voltage through a potentiometer and a signal output coupled with said light shield means, and a Zener diode trimming said Schmitt trigger to a practically constant threshold value.

3. A protective system according to claim 1 or claim 2, in which said electric circuit comprises signal switch means coupled with the electrode voltage which, independently of the absolute value of the electrode voltage and of the duration of a voltage reduction in the welding electrode circuit, is sensitive to a small reduction of the electrode voltage of the order of 1% of the electrode open circuit voltage to produce a light shield closing signal of sufficient duration to effect closing of the light shield before ignition of the arc.

4. A protective system according to claim 1 or 2, in which said electric circuit includes time delay circuit means including a capacitor to delay the opening of the light shield after the production of an opening signal by said threshold voltage switching means.

5. A protective system according to claim 1, in which said electric circuit comprises rectifying means having an input connected with said welding electrode circuit and producing at is output a direct current supply for components of said electric circuit.

6. A protective system according to claim 1, in which said light shield means comprises a shield movable in translation between open and closed position, spring means for moving said shield to closed position and two solenoids at opposite sides of said shield for moving said shield to open position when said solenoids are energized.

7. A protective system accoding to claim 6, in which each of two solenoids for moving said light shield comprises an armature plunger coupled with said light shield, a non-magnetic guide tube in which said plunger is slideable, and a coil wound around said non-magnetic tube.

8. A protective device according to claim 6 or 7 in which each of said solenoids has an iron magnetic circuit which, however, is not closed and is not in direct ferromagnetic connection with the armature in any position of the armature.

9. A protective system according to claim 6 or 7, comprising means for energizing said solenoids with an over-voltage during opening movement of said shield and thereafter supplying said solenoids with a reduced voltage only syfficient to hold the light shield in open position against the force of said spring means.

10. A protective system according to claim 1, in which means for coupling said electric circuit to the welding apparatus comprises two electric cables each having at one end means for releasably coupling said cable to said electric circuit and at the other end an insulating socket with a projecting sharp contact probe for penetrating the insulation of a welding electrode cable of said welding apparatus, said probe extending approximately parallel with and making contact with the conductor of said electrode cable.

11. A protective device according to claim 1, in which said electric circuit is housed in a casing mounted on or in said welding apparatus and said light shield means is mounted in a protective helmet or hand-held shield, and is connected with said electric circuit by a multi-conductor flexible cable having a covering resistant to temperatures up to 600° C.

12. A protective device according to claim 1, further comprising a microphone in a protective helmet near the user's mouth or a contact switch in a protective hand-held shield near the user's thumb for providing a signal to the input of said threshold voltage switching means to produce a closing signal for the protective light shield before ignition of the welding arc.

13. A protective device according to claim 2, in which means coupling the output of said Schmitt trigger with said light shield means comprises a switch transistor controlling a mini relay.

14. A protective device according to claim 1, in which said electric circuit comprises a signal switch circuit providing signals for controlling said electrically controlled light shield means and a control circuit coupled with said signal switch circuit and comprising said threshold value switching means.

15. A protective device according to claim 14, in which said signal switch circuit comprises an input, an output and an optical coupler between said input and output.

* * * * *